United States Patent
Gedeon

(10) Patent No.: US 6,302,851 B1
(45) Date of Patent: Oct. 16, 2001

(54) METHOD AND APPARATUS FOR DETERMINING A PULMONARY FUNCTION PARAMETER FOR GAS EXCHANGE

(75) Inventor: Andras Gedeon, Stockholm (SE)

(73) Assignee: Siemens-Elema AB, Solna (SE)

(*) Notice: Subject to any disclaimer, the term of this patent is extended or adjusted under 35 U.S.C. 154(b) by 0 days.

(21) Appl. No.: 09/554,441

(22) PCT Filed: Nov. 13, 1998

(86) PCT No.: PCT/SE98/02055

§ 371 Date: May 15, 2000

§ 102(e) Date: May 15, 2000

(87) PCT Pub. No.: WO99/25244

PCT Pub. Date: May 27, 1999

(30) Foreign Application Priority Data

Nov. 13, 1997 (SE) .................................... 9704159

(51) Int. Cl.[7] .................................................. A61B 5/08
(52) U.S. Cl. ........................... 600/538; 600/529; 600/532
(58) Field of Search ................................................ 600/538

(56) References Cited

U.S. PATENT DOCUMENTS 5,072,737 * 12/1991 Goulding ............................ 128/718

* cited by examiner

Primary Examiner—Robert L. Nasser
Assistant Examiner—Patricia C. Mallari
(74) Attorney, Agent, or Firm—Schiff Hardin & Waite

(57) ABSTRACT

A method and apparatus for determining a pulmonary function parameter, EVG, indicative of a living subject's effective lung volume, namely the lung volume in which gas exchange between respiratory air and pulmonary blood takes place efficiently. The apparatus carries out the steps of the method: (1) determining for a first breath during normal steady state breathing of the subject the end-tidal carbon dioxide or oxygen concentration $P_{et1}$ and the average rate of flow $V_{a1}$, over the duration $T_1$ of the breath, of expired carbon dioxide or oxygen, (2) determining for a second breath comprising a breath-hold period the end-tidal carbon dioxide or oxygen concentration $P_{et2}$ and the average rate of flow $V_{a2}$, over the duration $T_2$ of the breath, of expired carbon dioxide or oxygen, and (3) determining EVG as a quantity proportional to the ratio of the difference between said average flow rates $V_{a1}$ and $V_{a2}$ to the difference between said end-tidal concentrations $P_{et2}$ and $P_{et1}$.

13 Claims, 4 Drawing Sheets

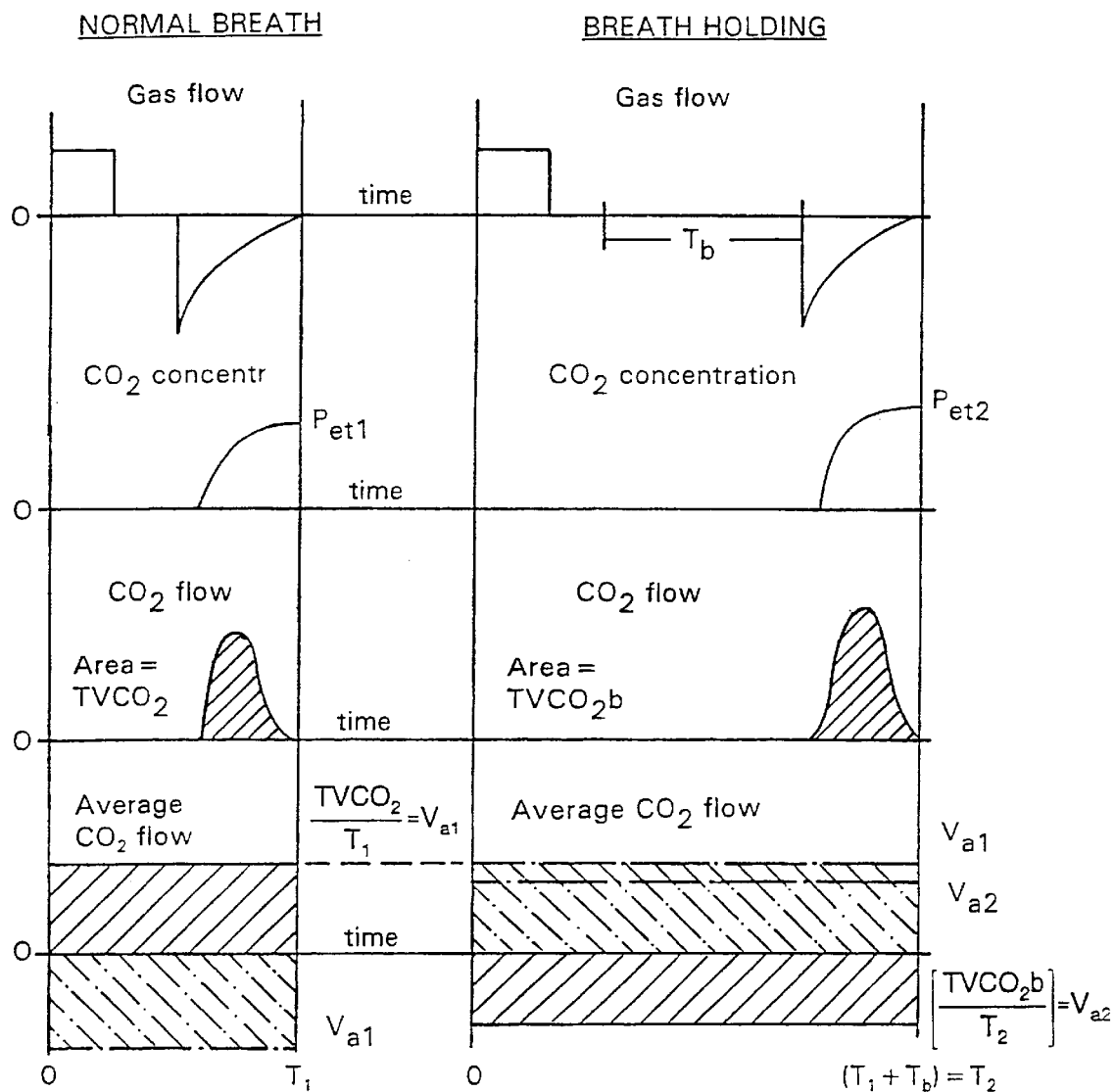

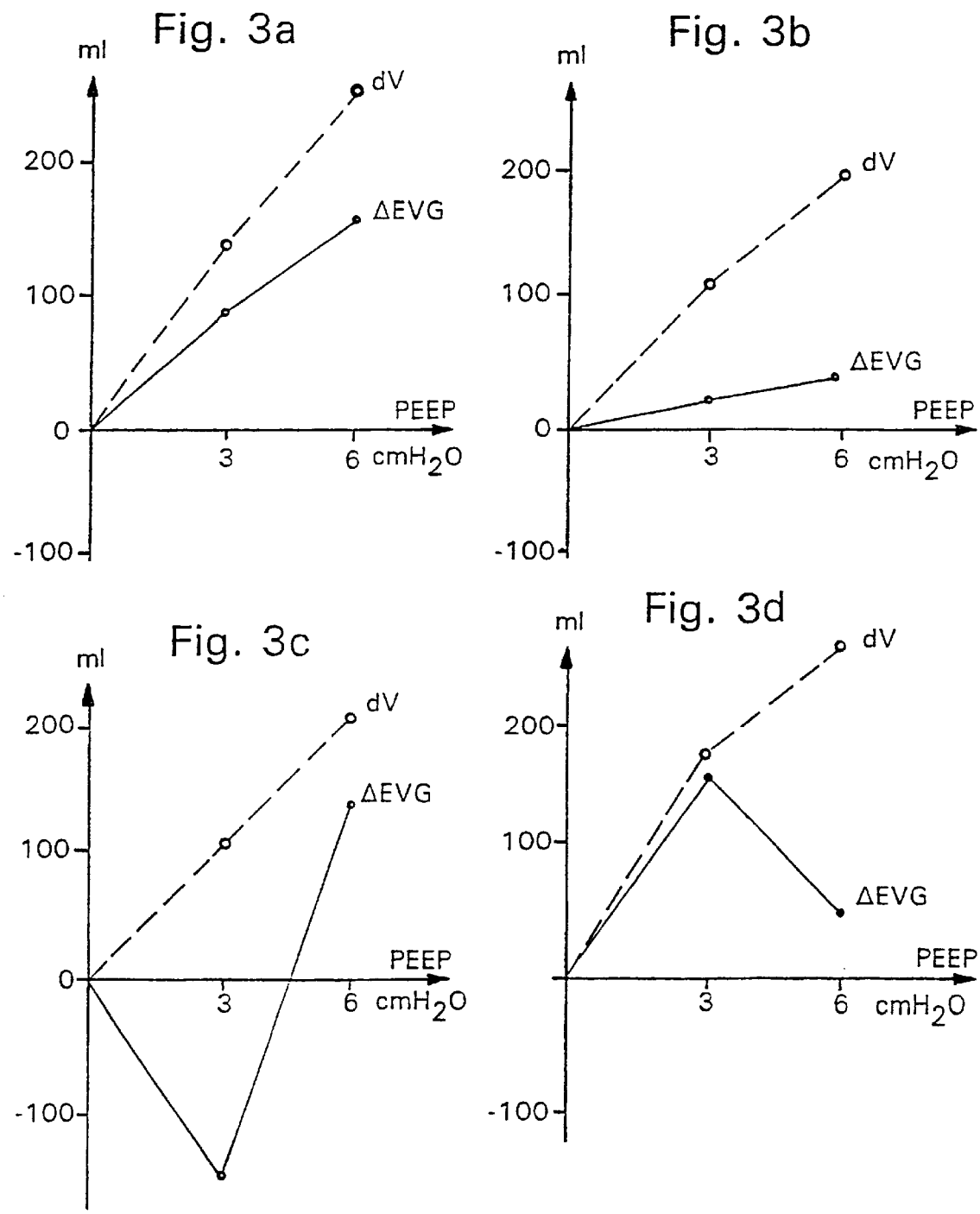

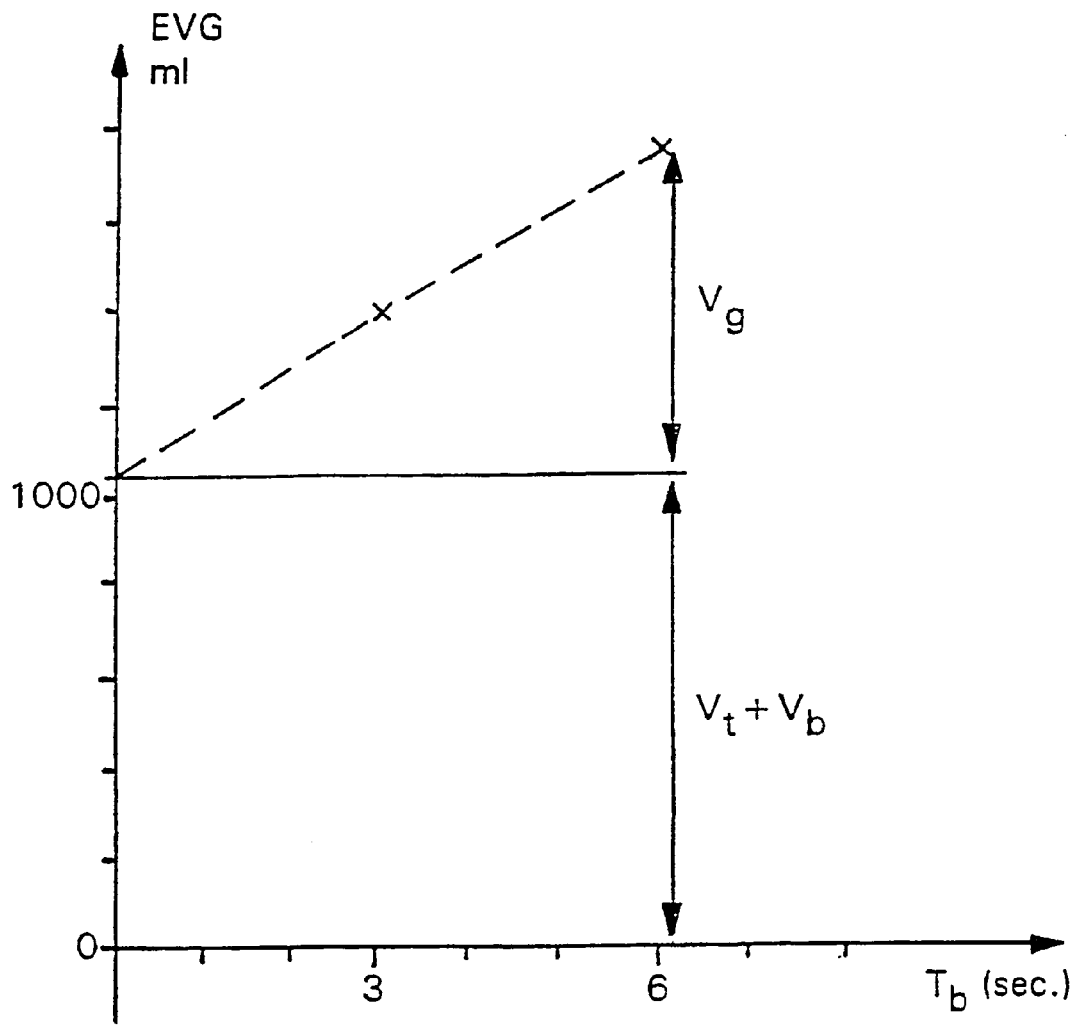

METHOD AND APPARATUS FOR DETERMINING A PULMONARY FUNCTION PARAMETER FOR GAS EXCHANGE

CROSS REFERENCE TO RELATED APPLICATION

The present application is the national stage under 35 U.S.C. 371 of PCT/SE98/02055, filed Nov. 13 1998.

This invention relates to a method and apparatus for determining a pulmonary function parameter, here abbreviated EVG, which is indicative of a living subject's effective lung volume, that is, the volume of the part-of the lungs which participates efficiently in the gas exchange between the respiratory gas and the pulmonary blood.

When a person is breathing spontaneously or is connected to an apparatus that provides artificial respiration, the ventilation of the lungs is characterised by the volume of the inspired gas, the so called tidal volume VT, and the breathing rate.

However, all of the gas making up the VT does not reach the finest structures, the alveoli, of the lungs where the exchange of gases takes place (oxygen being taken up by the pulmonary blood and carbon dioxide being released from the pulmonary blood into the gas phase). Moreover, part of VT gas may reach unperfused parts of the lungs and so will be unutilized because this part of the VT gas will have no contact with the pulmonary blood consequently will not take part in the gas-exchange process.

An important therapeutic goal in modern clinical care is to arrange for the best possible conditions for gas exchange in the lungs. The present invention addresses the problem how to assess the efficiency of the gas exchange. According to the invention an apparatus and a method are provided to measure this efficiency and a measure of the matching of ventilation with perfusion is given that can be used to guide therapy.

That portion of the VT gas which does not take part in the gas exchange process is called the dead space volume, VD, and the ratio of the dead space volume to the tidal volume is called the VD:VT fraction. The VD:VT fraction is routinely estimated in the clinical setting using measurements of the carbon dioxide partial pressures of the expired gas and the arterial blood. A description of the state of the art and a historical review of these methods are found in R. Fletcher "The single breath test for carbon dioxide" (1980) Thesis University of Lund Department of Anaesthesia and Clinical Physiology, Lund, Sweden. However, these methods are less than satisfactory because they rely only on measurements of carbon dioxide partial pressure and cannot therefore take into account the effects of both ventilation and circulation in the lungs. Methods based on the calculation of the VD:VT fraction therefore are not specific enough to guide therapy.

An alternative technique for estimating the effectiveness of the gas exchange process is to determine the fraction of the lung volume that participates fully in the gas-exchange process. Since carbon dioxide is soluble in lung tissue, the total volume of carbon dioxide in the lungs is made up of three parts, the gas volume in the alveoli of the lungs, $V_g$, and the gas volumes dissolved in the lung tissue, $V_t$, and in the pulmonary blood, $V_b$, respectively. The total volume is called the equivalent lung volume for carbon dioxide, abbreviated ELV, and can be estimated using carbon dioxide rebreathing techniques. (A Dubois: J Applied Physiology 5, 1, 1952; M Winsborough et al: Clinical Science 58,263 1980).

Although this approach does not have the same limitations as the VD:VT fraction techniques, the equivalent lung volume concept does not provide a sensitive measure of the effectiveness of the gas exchange process. This is so because of the inevitable gas mixing that takes place in the lungs of a person who breathes back and forth. This gas mixing tends to diminish the distinction between effective and ineffective lung areas. (M Petrini et al: J Appl. Phys. 53(4) 930 1982). In addition, the resulting distortion of information depends on the characteristics of the breathing pattern and/or the conditions of the rebreathing setup. Both systematic and random errors of measurement are introduced in this way.

The present invention provides a solution to these problems whereby a sensitive and specific assessment of the effective gas exchange volume in the lungs is possible. In addition, the measurement is simple and quick and can be performed non-invasively.

The invention will be fully understood from the following description with reference to the accompanying drawings.

FIGS. 2a and 2b are diagrams illustrating the method according to the invention and showing gas flow and concentration versus time for a normal breath (FIG. 2b) and a breath comprising a breath-hold period (FIG. 2b);

FIGS. 3a, 3b, 3c and 3d are four diagrams illustrating use of the method according to the invention as a guide for therapy.

FIG. 4 is a diagram showing how pulmonary tissue volume can be determined using the method according to the invention.

Figure 1:
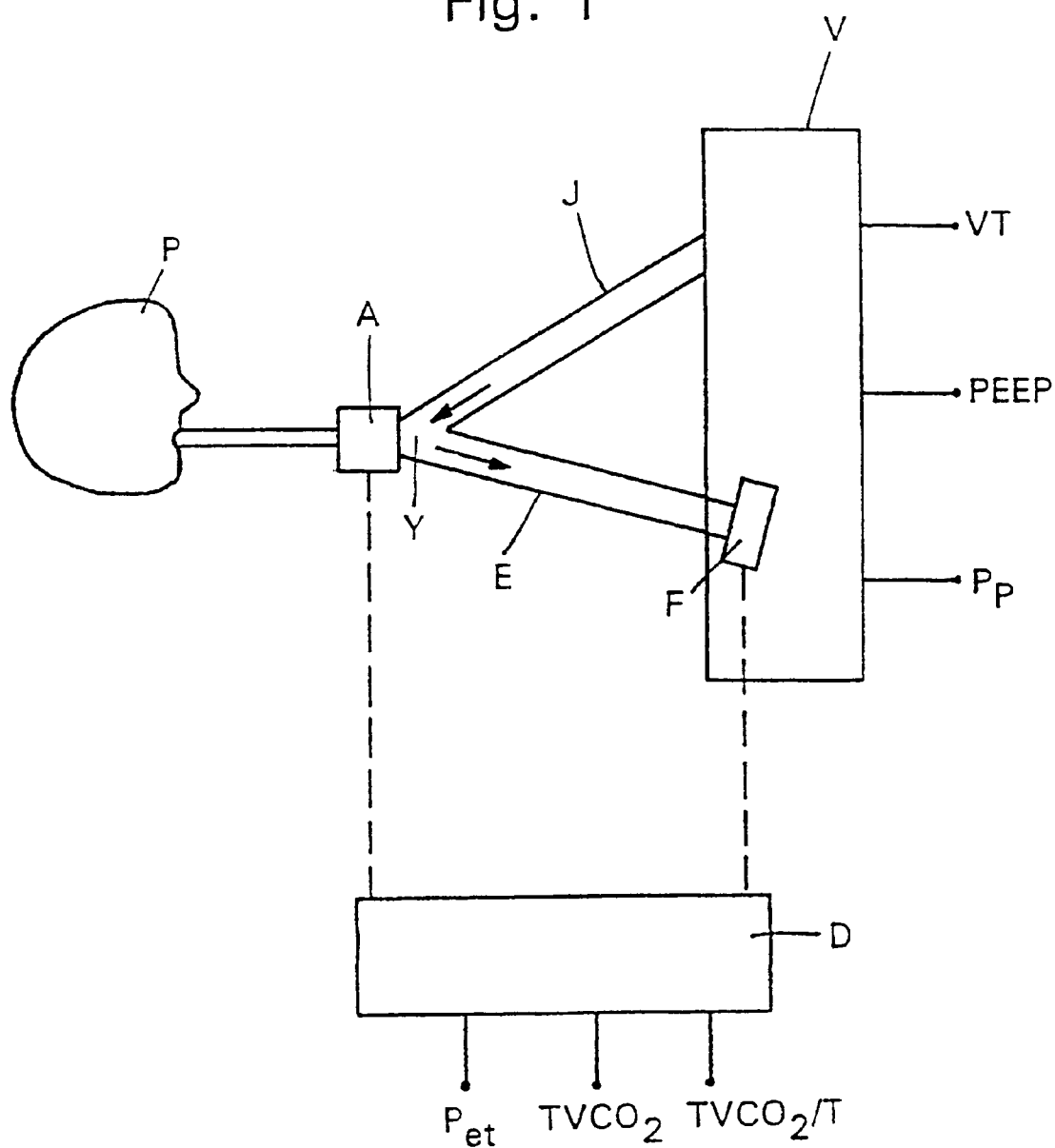
FIG. 1 is a schematic view showing a patient who breathes with the aid of a ventilator.

Referring to FIG. 1, a patient P is breathing spontaneously or with the aid of a ventilator V through an inspiratory breathing line J and an expiratory breathing line E. A standard fast-response carbon dioxide analyzer A (e.g. Capnomac AGM-103, Datex Instrumentarium Inc. Finland) is placed between the patient and the point Y where the inspiratory and expiratory lines meet. A flowmeter F, which may be a part of the ventilator (e.g. Servo Ventilator 900B), is placed in the expiratory breathing line to continuously record the expiratory flow from the patient. A data processing unit D collects the signal from the analyzer A and the flowmeter F and calculates the amount of carbon dioxide expired with each breath, TVCO2 [ml]. This is done by integration over time of the signal from the analyzer A and the flow signal from the flowmeter F. Typical graphs showing the flow of respiratory gas over a single normal breath and a breath comprising a breath-hold period are shown in FIGS. 2a and 2b.

In addition to the TVCO2 value, unit D also determines the end-tidal $CO_2$ concentration value, $P_{et}$ [%], that is, the carbon dioxide partial pressure measured at the very end of the expiration. This value is an indication of the carbon dioxide concentration as close to the blood-gas barrier as is possible using noninvasive means.

A specific example will illustrate the novel method.

The patient is breathing regularly at a rate of 15 breaths per minute, so that the duration of each breath is $T_1=4$ seconds.

Then the patient is caused to hold his breath for a short time $T_b$ after the end of the inspiratory phase of a breath to be observed, $T_b$ being 3 seconds, for example. If the patient is breathing with the aid of the ventilator V, the pause time between inspiration and expiration set on the ventilator (typically $0.25 \times T_1$ seconds) is increased in one breath by $T_b$ seconds (meaning in this example increased from 1 second to 4 seconds) so that the desired breath-hold period is implemented and the duration of the breath is extended to $T_2=7$ seconds. If the patient breathes spontaneously, the breath-hold period can be implemented simply by the patient holding his breath for the required time. After this single breath-hold manoeuvre the normal respiration pattern is resumed.

FIG. 2a shows typical respiratory flow patterns during normal breathing. FIG. 2b shows the corresponding conditions during the breath which comprises the breath-hold period.

The following typical values are obtained from unit D:

Normal breath: $TVCO2_1=12$ ml; $P_{et1}=5.0\%$

Breath-hold breath: $TVCO2_2=14$ ml; $P_{et2}=5.5\%$

In steady state breathing, that is, when the carbon dioxide leaving the pulmonary blood equals the expired carbon dioxide, the continuous carbon dioxide inflow from the pulmonary blood into the lungs thus is $TVCO2_1:T_1=12:4=3$ ml $CO_2$/s.

However, the expired carbon dioxide leaving the lungs after the breath-hold period corresponds to a continuous outflow from the lungs of $TVCO2_2:T_2=14:7=2$ ml $CO_2$/s.

The inflow being larger than the outflow, carbon dioxide is accumulated in the lungs at the blood/gas barrier during the breath that includes the breath-hold period. This is confirmed by the increase in the end-tidal $CO_2$ value $P_{et}$ from 5.0% to 5.5%. The effective lung volume associated with this increase of the end-tidal $CO_2$ value can be called EVG and is calculated as $$EVG = 100 \cdot T_2 \frac{\frac{TVCO2_1}{T_1} - \frac{TVCO2_2}{T_2}}{P_{et2} - P_{et1}} \quad (1)$$

If $V_{a1}$ and $V_{a2}$ are substituted for $TVCO2_1:T_1$ and $TVCO2_2:T_2$, respectively, as the designations for the average rate of flow of carbon dioxide over the durations $T_1$ and $T_2$ of the two breaths, Equation (1) can be rewritten as $$EVG = 100 \cdot T_2 \frac{V_{a1} - V_{a2}}{P_{et2} - P_{et1}} \quad (1')$$

EVG=1400 ml in the above example.

Equation (1) or (1') expresses EVG as a quantity which is proportional to the ratio of the difference in carbon dioxide flow rates to the difference in end-tidal carbon dioxide concentrations. It provides a sensitive indication of the effective lung volume because virtually no gas mixing takes place during the breath-hold manoeuvre.

EVG is also highly specific for the functional part of the lungs to be examined, because it does not include contributions from areas of the lungs that are ventilated but not perfused by blood, that is, areas where no carbon dioxide is released and, consequently, no contribution is made to the increase in the end-tidal carbon dioxide level $P_{et}$. Areas that have very little or no ventilation will not contribute either, because in these areas equilibrium between the carbon dioxide partial pressures in the blood and in the gas phase has been reached so that no carbon dioxide will pass through the blood/gas barrier.

Thus, EVG is a specific as well as sensitive measure of the functional part of the lungs in which the gas exchange is efficient.

It should be noted that in Equation (1) and (1') the time factor $T_2$ is included in order to provide a quantity EVG the dimension of which is volume (millilitre). If desired, $T_2$ can be omitted or replaced with some other time-based proportionality factor, because for practical purposes the usefulness of EVG resides in changes of EVG values ($\Delta$EVG), rather than in the actual numerical EVG values.

It should also be noted that in the EVG determination using Equation (1) as described above, it is possible to base the determination on a measurement of the oxygen uptake instead of, or in addition to, the carbon dioxide elimination. The only modification that is required is a substitution in Equation (1) of the values of the average oxygen flow rate for the values of the average carbon dioxide flow rate. Using the values of the average carbon dioxide flow rate is believed normally to be preferable if EVG determination only is required or desired, but as will become apparent below, EVG determination on the basis of the values of the average oxygen flow may also be useful.

The usefulness of the present invention, can be illustrated by reference to the well established clinical procedure in which the lungs is subjected to a positive end-expiratory pressure, PEEP, usually expressed in $cmH_2O$. This can be done by means of any modern ventilator, e.g. by closing the expiratory breathing line E before completion of the expiration, thereby trapping some air in the lungs so that the lungs remain somewhat overexpanded at the end of expiration. The elastic muscle forces acting to restore the original lung volume will therefore produce the desired PEEP pressure in the lungs. The compliance (stiffness) C of the lungs is defined in this case by the ratio C=dv:PEEP (ml/$cmH_2O$) wherein dV is the volume (ml) of air trapped in the lungs.

The same PEEP effect can be achieved in a spontaneously breathing person by introducing a suitable resistance to expiratory flow in the expiratory breathing line E.

For a patient connected to a ventilator, C can be calculated as $$C = \frac{VT}{P_p - PEEP} \quad (2)$$

where $P_p$ (pause pressure) is the pressure in the lungs immediately prior to the start of expiration. All the parameters in Equation (2) are readily available from a modern respirator (see FIG. 1). The purpose of PEEP therapy is to open collapsed lung segments, thereby to provide additional volumes in the lungs into which gas can enter and thereby to increase the effective volume for gas exchange. However, producing a pressure in the lungs may have negative effects as well. The most obvious of these is that the pressure will make it more difficult for the heart to pump blood through the lungs. Pulmonary blood flow may therefore decrease as a result of the application of PEEP, particularly in patients with a compromised circulatory state. A reduced blood flow can then be as detrimental to overall gas exchange as is a small effective lung volume. Evaluating PEEP therapy is therefore a high priority in the treatment of the severely ill patient.

FIG. 3 shows several cases where the new method and apparatus were used postoperatively on ventilated patients. Changes in EVG is in all cases compared with the expected mechanical expansion dV of the lungs resulting from increasing PEEP from 0 to 6 $cmH_2O$.

FIG. 3a shows a case with lungs of normal compliance of about 50 (ml/$cmH_2O$) where EVG increases with the expansion of the lungs as PEEP is increased from 0 to 6 $cmH_2O$. FIG. 3b shows a stiffer lungs where EVG remains nearly unaffected by the same increase in PEEP, indicating that the application of PEEP of this magnitude is of little or no benefit to the patient. FIG. 3c shows a case where there is an initial significant decrease in EVG for PEEP=3 cmH$_2$O followed by an impressive improvement for PEEP=6 cmH$_2$O. Finally, FIG. 3d shows a case where PEEP=3 cmH$_2$O clearly improves the effective gas exchange volume, but for PEEP=6 cmH$_2$O the negative effects of the pressure come into play and virtually eliminate the gain seen for PEEP=3 cmH$_2$O.

As is seen from these examples, one can define a dimensionless parameter, EG, for the efficiency of gas exchange, which is expected to be <1 and close to 1 when PEEP therapy works as intended. A therapeutic intervention, i.e. a change in PEEP level ($\Delta$PEEP) can be evaluated by the change produced in EVG ($\Delta$EVG) by calculating the value of EG from the equation $$EG = \frac{\Delta EVG}{VT} \cdot \frac{P_p - PEEP}{\Delta PEEP} \quad (3)$$

All parameters in Equation (3) can be easily measured noninvasively in the clinical setting.

Naturally, it is possible to determine EVG for different breath-hold times. FIG. 4 illustrates an example in which EVG has been determined according to Equation (1) or (1') for breath-hold times $T_b$ 3 seconds and 6 seconds.

Assuming that these breath-hold times are so short that there is no appreciable effect on the steady state carbon dioxide elimination, at least in the effective parts of the lungs, the change of the EVG with time can be treated as a linear process. Accordingly, the amount of carbon dioxide leaving the pulmonary blood can be regarded as proportional to the difference between the carbon dioxide partial pressure in the gas phase and that in the blood. It is therefore possible to extrapolate the EVG linearly back to $T_b$=0 as is indicated by the broken line in FIG. 4. Since it is known that it takes 0.5 seconds for carbon dioxide to reach equilibrium with lung tissue and pulmonary blood (R. Hyde et al: "Rate of Disappearance of Labeled Carbon dioxide from the Lungs of Human Beings during Breath Holding . . . ", The Journal of Clinical Investigation, Vol. 47, 1968, pp 1535–1552), the extrapolated EVG value for $T_b$=0 can be taken as a representation of only the tissue phase portion, $V_t$, plus the blood compartment portion, $V_b$ of the EVG.

Thus, the lung tissue volume, $V_t$, can be estimated from the EVG value, $EVG_6$, for $T_b$=6 seconds using the following equation $$V_t = EVG_6 - V_g - V_b \quad (4)$$

From FIG. 4 it is seen that $V_t + V_g = 1030$ ml in the illustrated exemplary case. Moreover, since the pulmonary blood volume, $V_b$, is normally only about 90 ml (R. Hyde et al: "Rate of Disappearance of Labeled Carbon dioxide from the Lungs of Human Beings during Breath Holding . . . ", The Journal of Clinical Investigation, Vol. 47, 1968, pp 1535–1552), an approximate value of $V_t$ can be obtained using the equation $V_t = EVG_6 - V_g 90$. Accordingly, in the exemplary case of FIG. 4, $V_t$ is approximately 940 ml.

In patients suffering from certain lung diseases, such as pulmonary edema and emphysema, the lung tissue volume is severely affected. Consequently, the method according to the invention as described with reference to FIG. 4 provides an indicator which is useful in monitoring and/or assessing therapy.

As is appreciated from the description of FIG. 4, the method for determining $V_t$ is based on the assumption that the change of EVG with time is sufficiently linear-to admit of a linear approximation. Actually, the change is non-linear, however, and the usefulness of the method therefore is limited to those instances in which a linear approximation produces results which are useful in spite of the inaccuracy caused by the nonlinearity of the EVG change with time.

An alternative, and more accurate, method for determining $V_t$ in accordance with the invention will now be described.

According to Hyde et al (cited above), carbon dioxide is equilibrated with lung tissue and capillary blood in about 0.5 s. Hence, the combined lung tissue and pulmonary blood volumes can be calculated, using Equation (1) and setting $T2=T_b+0,5$:

$$V_t + V_b = 100 \cdot (T_b + 0.5) \cdot \frac{V_{a1} - V_{a2}}{P_{et2} - P_{et/2}} \quad (5)$$

The total volume of carbon dioxide, including the volume resulting from the slow diffusion into gas and tissue compartments, can be calculated according to Hyde et al:

$$V_{Tot} = \frac{EVG}{1 - 0.55 \cdot e^{-0.725 \cdot Q_p \cdot T2}} \quad (6)$$

in which Qp is the pulmonary blood flow in liters per second and T2 is measured in seconds.

The gas compartment volume is $V_g = V_{Tot} - (V_t + V_b)$, and because $V_b$ is almost constant and small, about 90 ml, $V_{Tot}$ for a patient with Qp equal to, say, 0.067 l/s can be calculated from Equation (6): 2300 ml.

From Equation (5) it is seen that $V_t + V_b = 700$ ml, and with $V_b$=90 ml, $V_t$ will be=610. Finally, the gas compartment volume $V_g$=2300–1030=1270 ml.

It is important to note that it is also possible to determine the tissue volume, $V_t$, using EVG as measured by means of the oxygen uptake in the lung instead of by means of carbon dioxide elimination as described above. Equation (1) can be used, but instead of inserting the values of the carbon dioxide flows, the values of the oxygen inflow are used, and moreover the end-tidal values to be used are those for the oxygen partial pressures. Both the nominator and the denominator will change signs compared with the case where carbon dioxide values are used, and the EVG value will thus remain positive. Oxygen does not dissolve in pulmonary tissue, and the entire EVG value for oxygen, $EVG_{O2}$, measured in this way is therefore associated with $V_g$. Ignoring the insignificant difference between the volumes of $CO_2$ and $O_2$ dissolved in the blood, the following relationship applies:

$$V_t = EVG_{CO2} - EVG_{O2} \quad (7)$$

What is claimed is:

1. A method for determining a pulmonary function parameter, EVG, indicative of a living subject's effective lung volume, namely the lung volume in which gas exchange between respiratory air and pulmonary blood takes place efficiently, comprising the steps of determining for a first breath during normal steady state breathing of the subject the end-tidal concentration $P_{et1}$ of a given component of the respiratory air, said given component being one of carbon dioxide and oxygen, and the average rate of flow $V_{a1}$, over the duration $T_1$ of the breath, of the quantity of said given component expired during the breath, determining for a second breath comprising a breath-hold period the end-tidal concentration $P_{et2}$ of said given component and the average rate of flow $V_{a2}$, over the duration $T_2$ of the breath, of the quantity of said given component expired during the breath, determining EVG as a quantity proportional to the ratio of the difference between said average flow rates $V_{a1}$ and $V_{a2}$ of said given component to the difference between said end-tidal concentrations $P_{et2}$ and $P_{et1}$ of said given component.

2. A method according to claim 1 in which the breath-hold period separates the inspiration and the expiration of the second breath.

3. A method according to claim 1 in which the breath-hold period precedes the inspiration of the second breath.

4. A method according to claim 1 in which the duration of the breath-hold period is 1 to 15 seconds.

5. A method according to claim 1 in which the step of determining EVG is carried out using the equation $$EVG = 100 \cdot T_2 \frac{(V_{a1} - V_{a2})}{(P_{et2} - P_{et1})} \qquad (1')$$

in which $V_{a1}$, $V_{a2}$, $P_{et1}$, $P_{et2}$ and $T_2$ are the same quantities as above.

6. A method according to claim 1 in which the subject breathes spontaneously.

7. A method according to claim 1 in which the subject breathes with the aid of a ventilator.

8. A method according to claim 1 which comprises the additional step of determining the change of the subject's EVG as a function of positive end-expiratory pressure, PEEP, of the subject's lungs.

9. A method for determining lung tissue volume, $V_t$, of a living subject, comprising the steps of determining the values of the subject's EVG in accordance with claim 1 for two different non-zero breath-hold durations, determining by linear extrapolation from the EVG values so determined a value of the subject's EVG for zero breath-hold duration, and determining the $V_t$ of the subject from the known relationship of $V_t$ to said EVG value for zero breath-hold duration and the EVG value for a non-zero breath-hold duration.

10. A method for determining lung tissue volume, $V_t$, of a living subject, comprising the steps of determining the value, $EVG_{CO2}$, of the subject's EVG in accordance with claim 1 using carbon dioxide as said given component of the respiratory gas, determining the value, $EVG_{CO2}$, of the subject's EVG in accordance with claim 1 using oxygen as said given component of the respiratory gas, determining $V_t$ from the equation $$V_t = EVG_{CO2} - EVG_{O2} \qquad (7).$$

11. A device for determining a pulmonary function parameter, EVG, indicative of a living subject's effective lung volume, namely the lung volume in which gas exchange between respiratory air and pulmonary blood takes place efficiently, comprising means for determining for a first breath during normal steady state breathing of the subject the end-tidal concentration $P_{et1}$ of a given component of the respiratory gas, said given component being one of carbon dioxide and oxygen, and the average rate of flow $V_{a1}$, over the duration $T_1$ of the breath, of the amount of said given component expired during the breath, means for determining for a second breath comprising a breath-hold period the end-tidal concentration $P_{et2}$ of said given component and the average rate of flow $V_{a2}$, over the duration $T_2$ of the breath, of the amount of said given component expired, means for determining EVG as a quantity proportional to the ratio of the difference between said average flow rates $V_{a1}$, and $V_{a2}$ to the difference between said end-tidal concentrations $P_{et2}$ and $P_{et1}$.

12. Apparatus according to claim 11 including means for determining EVG using the equation $$EVG = 100 \cdot T_2 \frac{(V_{a1} - V_{a2})}{(P_{et2} - P_{et1})} \qquad (1')$$

in which $V_{a1}$, $V_{a2}$, $P_{et2}$, $P_{et2}$ and $T_2$ are the same quantities as above.

13. Apparatus according to claim 11 including means for determining the change, $\Delta EVG$, of the subject's EVG as a function of positive end-expiratory pressure, PEEP, of the lungs of the subject.

* * * * *